US012751857B1

(12) United States Patent
Horváth et al.

(10) Patent No.: US 12,751,857 B1
(45) Date of Patent: Oct. 6, 2026

(54) PATIENT WARMING PAD HAVING A TEMPERATURE SENSOR AT INTENDED PATIENT-NON-CONTACT REGIONS

(71) Applicant: GENTHERM MEDICAL, LLC, Cincinnati, OH (US)

(72) Inventors: Zoltán Horváth, Budapest (HU); Zoran Panic, Windsor (CA); Wladimir Kukuruza, Augsburg (DE); Igor Spasojevic, Belle River (CA)

(73) Assignee: Gentherm Medical, LLC, Cincinnati, OH (US)

( * ) Notice: Subject to any disclaimer, the term of this patent is extended or adjusted under 35 U.S.C. 154(b) by 0 days.

(21) Appl. No.: 19/428,724

(22) Filed: Dec. 22, 2025

Related U.S. Application Data

(60) Provisional application No. 63/906,751, filed on Oct. 28, 2025.

(51) Int. Cl.
*A61F 7/08* (2006.01)
*A61F 7/00* (2006.01)

(52) U.S. Cl.
CPC ................ *A61F 7/08* (2013.01); *A61F 7/007* (2013.01); *A61F 2007/0005* (2013.01); *A61F 2007/003* (2013.01); *A61F 2007/0096* (2013.01)

(58) Field of Classification Search
CPC .... A61F 7/08; A61F 7/007; A61F 2007/0005; A61F 2007/003; A61F 2007/0096; A61F 2007/0018; A61F 2007/0095
USPC ........................................................ 607/109
See application file for complete search history.

(56) References Cited

U.S. PATENT DOCUMENTS

| | | | |
|---|---|---|---|
| 6,924,467 | B2 | 8/2005 | Ellis et al. |
| 11,266,525 | B2 | 3/2022 | Kaforey et al. |
| 2006/0020311 | A1 | 1/2006 | Ellis et al. |
| 2006/0118541 | A1 | 6/2006 | Ellis et al. |
| 2008/0255641 | A1 | 10/2008 | Ellis |
| 2011/0233185 | A1 | 9/2011 | Augustine et al. |
| 2013/0174854 | A1 | 7/2013 | Pigazzi et al. |
| 2021/0236326 | A1 | 8/2021 | Nardo et al. |

FOREIGN PATENT DOCUMENTS

| | | | | |
|---|---|---|---|---|
| WO | WO-2012125916 A2 * | 9/2012 | .......... | A61F 7/0097 |
| WO | WO-2016147115 A1 * | 9/2016 | ............ | A61F 7/007 |
| WO | WO-2023283188 A1 * | 1/2023 | .......... | A47C 21/048 |

* cited by examiner

*Primary Examiner* — Beverly M Flanagan
(74) *Attorney, Agent, or Firm* — The Dobrusin Law Firm, P.C.

(57) ABSTRACT

A patient warming pad configured for placement between a patient and a support surface of a medical table. The warming pad includes a body having a top layer and a bottom layer. The top layer defines an intended patient-contact region and an intended patient-non-contact region, and the bottom layer defines a support-contact region. A heating device, including a heating element configured to generate heat, is disposed between the top and bottom layers and extends below at least a portion of both the intended patient-contact region and the intended patient-non-contact region. One or more temperature sensors are positioned on the heating device such that the sensors are located below the intended patient-non-contact region.

19 Claims, 2 Drawing Sheets

PATIENT WARMING PAD HAVING A TEMPERATURE SENSOR AT INTENDED PATIENT-NON-CONTACT REGIONS

CROSS-REFERENCE TO RELATED APPLICATIONS

This application claims priority to U.S. 63/906,751 filed on Oct. 28, 2025, the entirety of which is hereby incorporated by reference herein in its entirety for all purposes.

FIELD

These teachings relate to patient support pads for use in medical or surgical procedures, and more particularly to a patient support pad having one or more temperature sensors in one or more intended patient-non-contact regions.

BACKGROUND

Some medical procedures require a patient to be supported on a medical table. A support pad may be positioned between the patient and the medical table to help maintain the patient in a desired position, enhance comfort, and reduce the risk of pressure-related injuries.

Some support pads include a heating device configured to warm the patient or increase the patient's body temperature before, during, or after a medical procedure to help maintain normothermia (i.e., normal body temperature). Maintaining patient normothermia is important to prevent complications during and after surgery. For instance, a drop in core body temperature can result in hypothermia, which may prolong recovery and increase the risk of adverse outcomes such as excessive bleeding, infection, postoperative shivering, and cardiac complications.

Some patient warming pads include one or more temperature sensors positioned under the patient to monitor temperature. Sensor placement under a patient may however create localized pressure points that affect patient comfort, may be located in regions where fluids (e.g., blood, saline, irrigation, etc.) can pool during a medical procedure, and some sensors or associated wiring may be radiopaque, resulting in unwanted image artifacts during X-ray procedures.

Accordingly, there is a need for an improved patient warming pad having one or more temperature sensors that are located or positioned at one or more intended patient-non-contact regions, outside of one or more intended patient-contact regions, in one or more areas where fluids are less likely to pool, and/or where the one or more sensors and associated wiring do not appear on X-ray imaging. Such configurations may improve patient comfort while maintaining accurate temperature monitoring and imaging compatibility.

SUMMARY

These teachings provide a patient warming pad, system, and related methods of making and using a patient warming pad and system.

The patient warming pad is configured for placement between a patient and a support surface of a medical table. The patient warming pad includes a body having a top layer and a bottom layer. The top layer has a top surface that defines one or more intended patient-contact regions and one or more intended patient-non-contact regions. The bottom layer has a bottom surface that defines a support-contact region. A heating device, that includes one or more heating elements, and is configured to generate heat, is disposed between the top and bottom layers, and extends below at least a portion of one or more of the intended patient-contact regions and one or more of the patient-non-contact regions. One or more temperature sensors are positioned on the heating device and below the top layer such that the one or more sensors is/are located at or below one or more of the intended patient-non-contact regions. One or more of the temperature sensors are positioned on the heating device and under the top layer such that the one or more temperature sensors is/are not located at or below one or more of the intended patient contact regions.

These teachings provide a method of making a patient warming pad configured for placement between a patient and a support surface of a medical table. The method includes one or more steps. The method may include forming a body comprising a top layer and a bottom layer, the top layer having a top surface that defines an intended patient-contact region and an intended patient-non-contact region. The bottom layer has a bottom surface that defines a support-contact region. The method may include providing a heating device comprising a heating element configured to generate heat and one or more temperature sensors to measure temperature. The method may include positioning the heating device between the top layer and the bottom layer such that the heating device extends below at least a portion of both the intended patient-contact region and the intended patient-non-contact region, the one or more temperature sensors are located below the intended patient-non-contact region, the one or more temperature sensors are not located below the intended patient-contact region.

The body, the top layer, and/or the bottom layer may comprise foam.

The patient warming pad according to these teachings advantageously allows for accurate temperature sensing without introducing pressure points in patient-contact regions of the pad, reduces the likelihood of sensor exposure to fluids, and minimizes interference with X-ray imaging.

DETAILED DESCRIPTION

Figure 1:
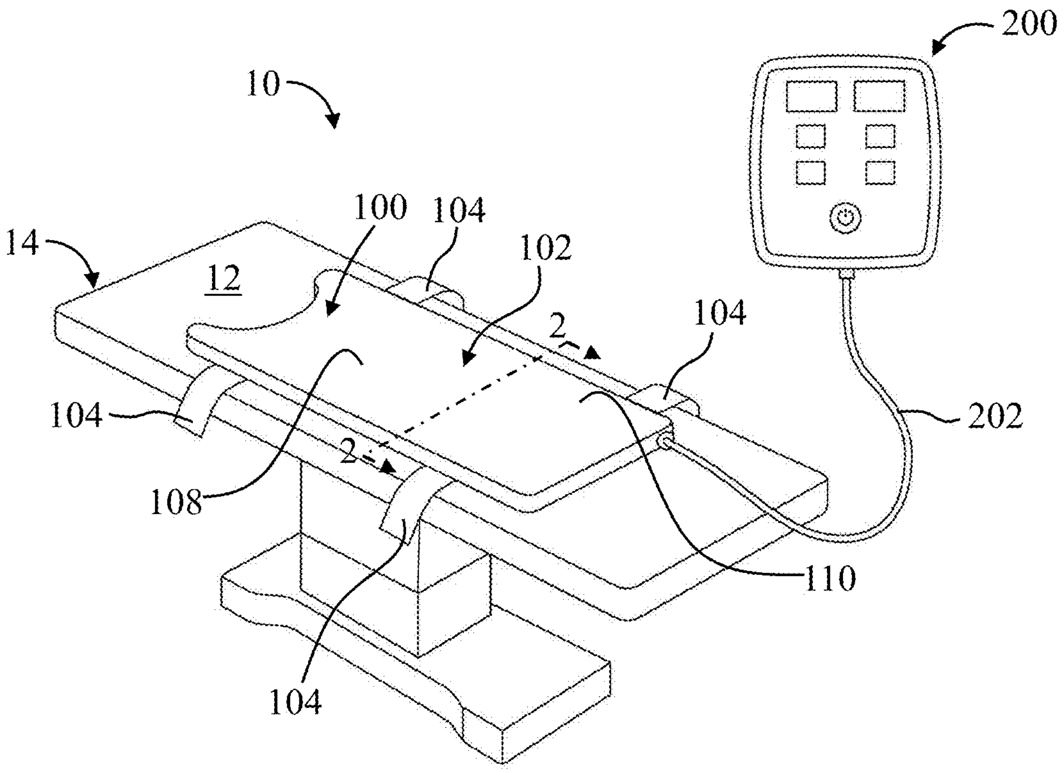
FIG. 1 is a perspective view of a patient warming pad on a medical table.

FIG. 1 illustrates a patient warming system 10. The patient warming system 10 comprises a patient warming pad 100 and a control device 200. The patient warming pad 100 may be configured for placement or arrangement on a support surface 12 of a medical table 14. In some configurations, the medical table 14 can be part of the system 10.

The patient warming pad 100 generally comprises a body 102 and one or more straps 104 for securing the patient warming pad 100 or body 102 to the medical table 14 and/or for securing a patient to the pad 100 and/or to the medical table 14.

Figure 2:
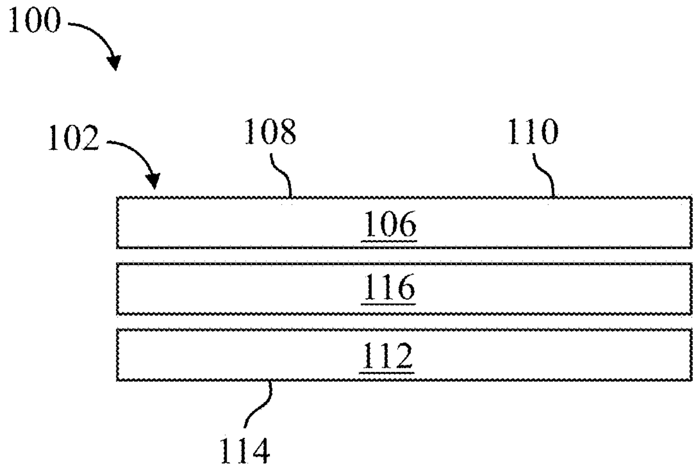
FIG. 2 is a cross sectional view of a patient warming pad taken along line 2-2 in FIG. 1.

With additional reference to FIG. 2, a schematic illustration of the patient warming pad 100 taken along line 2-2 in FIG. 1 is shown. The body 102 comprises a top layer 106 having a top surface that has or defines one or more intended patient-contact regions 108 and one or more intended patient-non-contact regions 110. The body 102 comprises a bottom layer 112 having a bottom surface that has or defines a support-contact region 114.

The body 102, the top layer 106, and/or the bottom layer 112 may be or may comprise foam. In other words, the body 102 may be a foam body, the top layer 106 may be a top foam layer, and/or the bottom layer 112 may be a bottom foam layer.

During use, a patient may be positioned on or against the top surface of the top layer 106. More specifically, during use, a patient or one or more body parts of a patient are intended to be positioned on, in contact with, or apply pressure against one or more intended patient-contact regions 108 on the top surface of the top layer 106. During use, a patient or one or more body parts of a patient are not intended to be positioned on, in contact with, or apply pressure against one or more intended patient-non-contact regions 110 on the top surface of the top layer 106. The bottom surface or the support-contact region 114 of the bottom layer 106 may be positioned on or against the support surface 12 of the medical table 14.

A heating device or heating layer 116 may be disposed within the body 102 between the top layer 106 and the bottom layer 112. The heating device 116 is configured to generate and provide heat to warm one or more regions or zones of the pad 100 to deliver warmth to certain corresponding zones or areas of a patient's body. Elements of the heating device 116 may be electrically connected to the control device 200 via one or more cables 202 for operating, monitoring, and controlling the heating device 116.

Figure 3:
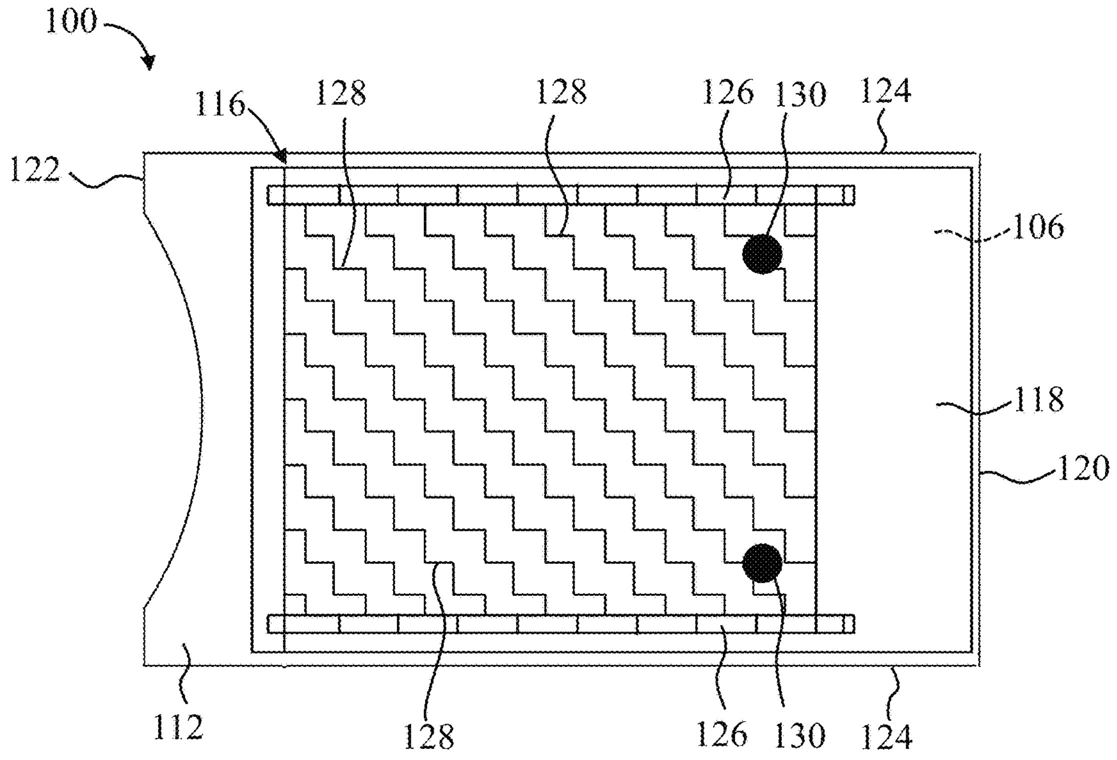
FIG. 3 is a top view of a patient warming pad with the top layer shown in transparent to illustrate underlying components of the pad.

FIG. 3 illustrates a patient warming pad 100, with the top layer 106 shown in transparent to illustrate underlying components of the heating device 116, the bottom layer 112, and pad 100.

The heating device 116 comprises a flexible, sheet-like carrier or substrate 118. The carrier or substrate 118 extends substantially between a head end 120 of the pad 100 and a tail end 122 of the pad 100. A head end 120 of the pad 100 may be a region, side, edge, or end of the pad 100 where a patient's head is intended to be positioned before or during a medical procedure. A tail end 122 of the pad 100 may at an opposite side, edge, or end of the pad 100 from the head end 120, and may be a region or side or end of the pad 100 where a patient's lower back or buttocks is positioned before or during a medical procedure. A perineal cutout (e.g., a cutout, or a U-shaped or half-moon cutout) may be defined at the tail end 122 of the pad 100. The perineal cutout defined in the pad 100 may provide clearance for drainage devices, imaging probes, or surgical instruments and provide access to a patient's perineal or pelvic region during procedures such as gynecological, urological, rectal, or colorectal surgeries. The carrier or substrate 118 extends substantially between the opposing lateral sides 124 of the pad 100.

The heating device 116 comprises a pair of spaced-apart conductive bus bars 126. The bus bars 126 may be supported on the substrate 118 and arranged adjacent to the lateral sides 124 of the pad 100.

The heating device 116 comprises one or more heating elements 128. The one or more heating elements 128 may be supported on the substrate 118 and extend between and are electrically coupled to the opposing bus bars 126 to complete an electrical circuit across the heating device 116. The one or more heating elements 128 may comprise one or more resistive wires, carbon wires, carbon filaments, carbon strands, a resistive or conductive fabric or ink, or a combination thereof. The bus bars may be electrodes.

The heating device 116 may comprise one or more temperature sensors 130. The one or more temperature sensors 130 may be configured to detect a temperature generated by the heating device 116 and/or one or more heating elements 128 and/or a temperature of the heating layer and/or one or more layers of the pad. The one or more temperature sensors 130 may be configured to detect an ambient temperature surrounding the heating device 116 and/or heating elements 128.

During use, when electrical power is supplied to the heating device 116 from, for example, the control device 200, through one or more cables 202 (see FIG. 1), the electrical power can be applied across the bus bars 126, causing current to flow through the heating elements 128. The heating elements 128 have an electrical resistance that generates heat in response to the current. The generated heat is conducted through at least the top layer 106 to warm or provide heat to a patient supported on the pad 100. The one or more temperature sensors 130 may be configured to detect a temperature generated by the heating device 116 and/or one or more heating elements 128. Data or signals from the one or more temperature sensors 130 may be provided as feedback to the control device 200 for regulating the heating device 116.

The control device 200 may be configured to regulate power supplied to the one or more heating element 128 based on signals related to the temperature of the heating device 116 received from the one or more temperature sensors 130. For example, the control device 200 may be configured to maintain a temperature of at least the intended patient-contact surface 108 within a range of approximately 35° C. to 42° C. The control device 200 may be configured to deactivate the heating device 116 and/or the one or more heating elements 128 in response to detecting a temperature exceeding a predetermined safety threshold.

The one or more temperature sensors 130 may be or may comprise one or more negative temperature coefficient (NTC) temperature sensors. The heating device 116 may comprise two temperature sensors 130. The heating device 116 may comprise exactly two temperature sensors 130. The heating device 116 may comprise no more than two temperature sensors 130. In some instances, the heating device 116 may comprise more than two temperature sensors 130 or less than two temperature sensors 130 (e.g., only one temperature sensor).

Figure 4:
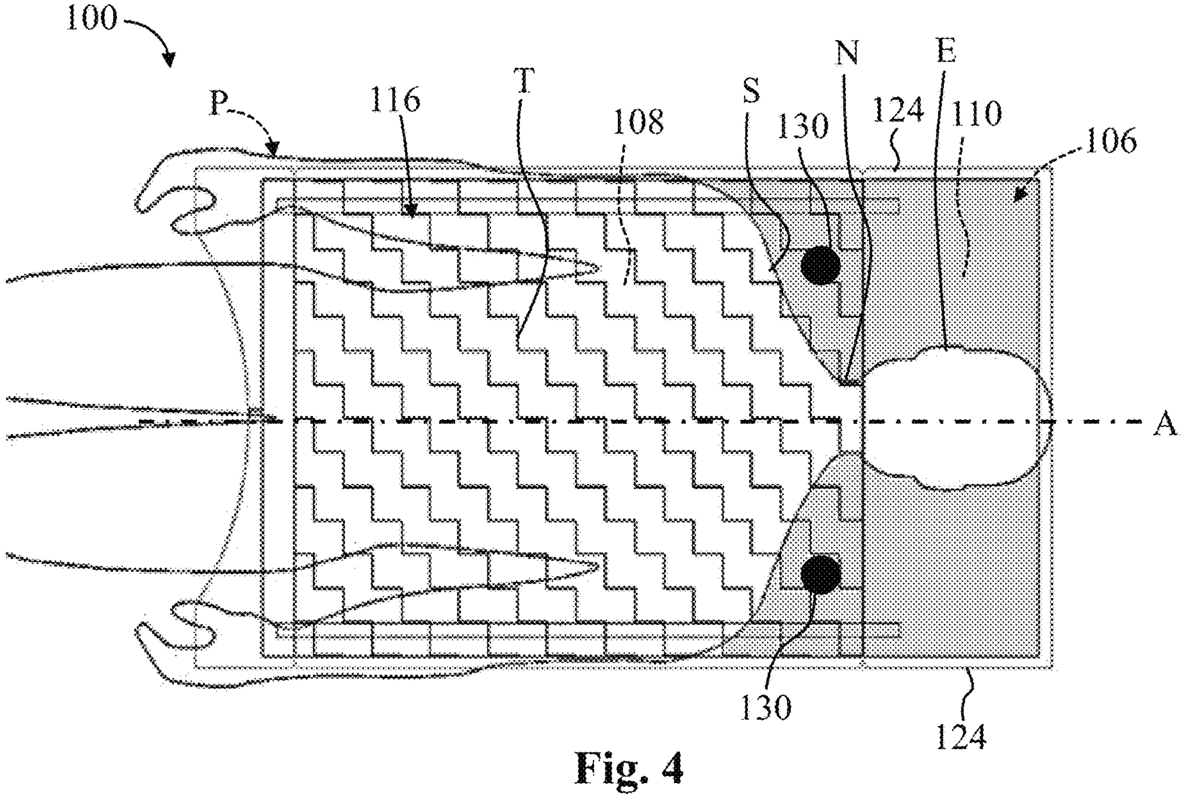
FIG. 4 is a top view of a patient warming pad with a patient and the top layer of the pad shown in transparent to illustrate underlying components of the pad.

With additional reference to FIG. 4, the pad 100 is shown with both the top layer 106 and the patient P in transparent to illustrate underlying components of the heating device 116 and pad 100.

The pad 100 or top layer 106 may comprise a top surface having one or more intended patient-contact regions 108 and one or more intended patient-non-contact regions 110.

One or more of the intended patient-contact regions 108 of the pad 100 may be located under or adjacent to an outline or perimeter of the patient P that is positioned or intended to be positioned on the pad 100. An intended patient-contact region 108 may be one or more areas, regions, zones, or parts of the body 102 or top layer 106 where a patient or one or more body parts of a patient is intended to be positioned or in contact with or apply pressure onto the top layer 106 before or during a medical or surgical procedure. For example, an intended patient-contact region 108 may be one or more areas, regions, zones, or parts of the body 102 or top layer 106 where a patient's head, neck, shoulders, torso, back, arms, waist, are located or positioned on the pad 100 or top layer 106. An intended patient-contact region 108 may be one or more areas, regions, zones, or parts of the body 102 or top layer 106 where fluids (e.g., blood, irrigation, etc.) typically can pool during a medical procedure. An intended patient-contact region 108 may be one or more areas, regions, zones, or parts of the body 102 or top layer 106 that may be included in X-ray imagery.

One or more of the intended patient-non-contact regions 110 of the pad 100 may be located outside of or adjacent to an outline or perimeter of one or more body parts of the patient P that is positioned or intended to be positioned on the pad 100. An intended patient-non-contact region 110 may be one or more areas, regions, zones, or parts of the body 102 or top layer 106 where a patient or one or more body parts of a patient is not intended to be positioned or intended to not be contact with or does not apply pressure onto the top layer 106 before or during a medical procedure. For example, an intended patient-non-contact region 110 may be one or more areas, regions, zones, or parts of the pad 100 where a patient's head, neck, shoulders, torso, back, arms, waist, are not intended to be located or positioned on the pad 100 or top layer 106. An intended patient-non-contact region 110 may be one or more areas, regions, zones, or parts of the body 102 or top layer 106 where fluids (e.g., blood, irrigation, etc.) do not typically pool during a medical procedure. An intended patient-non-contact region 110 may be one or more areas, regions, zones, or parts of the body 102 or top layer 106 that are not included in X-ray imagery. In the interest of contrast, one or more of the intended patient-non-contact regions 110 are shaded in grey in FIG. 4.

The one or more temperature sensors 130 may be located or positioned on the heating device 116 such that the one or more temperature sensors 130 are located at or below one or more of the intended patient-non-contact regions 110 of the pad 100. In other words, the one or more temperature sensors 130 are not positioned on the heating device 116 so that the one or more temperature sensors are located at or below one or more of the intended patient-contact regions 108 of the pad 100.

The heating device 116 may be dimensioned and arranged within the body 102 such that the one or more temperature sensors 130 are located at or below one or more of the intended patient-non-contact regions 110 of the pad 100. The heating device 116 may be dimensioned and arranged within the body 102 such that the one or more temperature sensors 130 are not located at or below one or more of the intended patient-contact regions 108 of the pad 100.

More specifically, before or during use, a patient P, or one or more body parts of a patient P are intended to be positioned on, in contact with, or apply pressure against or onto one or more of the intended patient-contact regions 108 of that pad 100 that do not include any temperature sensors 130 below the patient or those regions 108 of the pad.

Before or during use, a patient P, or one or more body parts of a patient, are not intended to be positioned on, in contact with, or apply pressure against or onto one or more of the intended patient-non-contact regions 110 on the top surface of the top layer 106 that include one or more temperature sensors 130 below those regions 110 of the pad.

Advantageously, sensor 130 placement in one or more of the intended patient-non-contact regions 110 may avoid creating localized pressure points that affect patient comfort, may be outside of regions where fluids (e.g., blood, irrigation, etc.) can pool during a medical procedure, and may be outside of regions that may result in unwanted image artifacts during X-ray procedures.

Moreover, sensor 130 placement in one or more of the intended patient-non-contact regions 110 may enable more reliable temperature measurements because the patient is not compressing the body or top layer against the sensor 130, which may change or affect heat transmission from the one or more heating elements and affect the temperature measurement.

The one or more temperature sensors 130 and/or the one or more intended patient-non-contact regions 110 may be laterally offset from a central longitudinal axis A of the heating device 116 or pad 100. The one or more temperature sensors 130 and/or the one or more intended patient-non-contact regions 110 may be arranged approximately 5 cm (or more than 5 cm or less than 5 cm) from the opposing sides or edges 124 of the pad 100. The one or more temperature sensors 130 and/or the one or more intended patient non-contact regions 110 may be arranged more than approximately 247 mm from the head end 120 of the body 102.

The one or more temperature sensors 130 and/or the one or more intended patient-non-contact regions 110 may be located above a shoulder region S of the patient when the patient is positioned on or in the one or more intended patient-contact regions 108. The one or more temperature sensors 130 and/or the one or more intended patient-non-contact regions 110 may be located between a shoulder region S and an ear region E of the patient P (relative to or along the axis A) when the patient P is positioned on or in the one or more intended patient-contact regions 108. The one or more temperature sensors 130 and/or the one or more intended patient-non-contact regions 110 may be located between a shoulder region S and a neck region N of the patient P (relative to or along the axis A) when the patient P is positioned on or in the one or more intended patient-contact regions 108. The one or more temperature sensors 130 may be located on opposite sides of the longitudinal axis A. The one or more temperature sensors 130 may be symmetrically arranged on the substrate or heating layer relative to the longitudinal axis A.

The heating device 116 and/or the one or more intended patient-contact regions 108 may be free of any temperature sensors 130 in or under a torso region T of the patient. The heating device 116 and/or the one or more intended patient-non-contact regions 110 may be free of or omit or not include any temperature sensors 130 below a shoulder region S of the patient, neck region N of the patient, below the arms of the patient, below the head of a patient, below a back of a patient, or any combination thereof.

Referring to the FIGS. 1-4, a method of making a patient warming pad 100 configured for placement between a patient and a support surface of a medical table 14 is disclosed. The method includes one or more steps of: forming a body 102 comprising a top layer 106 and a bottom layer 112. The top layer 106 may define an intended patient-contact region 108 and an intended patient-non-contact region 110. The bottom layer 112 may define a support-contact region 112. The method may include providing a heating device or layer 116 comprising a heating element 128 configured to generate heat and one or more temperature sensors 130 to measure temperature. The method may include positioning the heating device 116 between the top layer 106 and the bottom layer 112 such that the heating device 116 extends below at least a portion of both the intended patient-contact region 108 and the intended patient-non-contact region 110. The one or more temperature sensors 130 may be located below the one or more intended patient-non-contact regions 110.

The body 102, the top layer 106, and/or the bottom layer 112 may be or may comprise foam. In other words, the body 102 may be a foam body, the top layer 106 may be a top foam layer, and/or the bottom layer 112 may be a bottom foam layer.

It is understood that the method steps disclosed herein can be performed in virtually any order and are not necessary to be in the order disclosed herein unless otherwise noted. One or more of the steps can be combined with one or more other steps; one or more steps can be omitted or eliminated; one or more steps can be repeated or duplicated; one or more steps can be split into two or more steps; one or more of the steps can be rearranged in a different order relative to other method steps; or any combination hereof.

While the teachings herein are directed to a patient warming pad configured for placement between a patient and a support surface of a medical table is disclosed, the teachings may be applied to a patient warming blanket. Such a blanket may be provided over a patient that is supported on a pad and/or medical table. The blanket may include one or more of any of the elements disclosed herein, including one or more heated and non-heated zones, one or more reference indicators, etc.

In other configurations, the teachings herein may be directed to a pad or blanket that can be used in non-medical environments, such as home, office, etc.

The one or more temperature sensors may be configured for measuring a temperature of the body which is warmed by the heating element. The one or more temperature sensors may be operatively connected to the control device via power and/or signal leads and provide temperature data of the heating element or warming pad to a processor associated with the control device for controlling or regulating the thermal element(s) and/or to provide temperature data of the heating element or warming pad to a processor associated with the control device. Temperature data obtained by the one or more temperature sensors may be displayed on control device, and be used by operating room staff to maintain the temperature of warming pad within a safe temperature range. In some examples, a suitable temperature range for the pad 100 is between about 37° C. and 42° C. Temperature data from the one or more temperature sensors also may be used by a processor in the control device to automatically monitor the warming pad and maintain the temperature thereof within the safe range. The processor may also cause the control device to provide a notification and/or warning to a user if a measured temperature is greater than a maximum allowable temperature or target value. The control device may be configured to allow operating room staff to control power to the heating element, and to receive and read temperature data from the temperature sensors. In an embodiment, control device may include a processor programmed to automatically control the temperature of the heating element based on data returned from temperature sensors. The processor of the control device is configured to receive signals representative of a temperature of the warming pad from the temperature sensors. The processor may be configured to determine an average temperature value or, in other cases, may record temperature values for different areas of the pad. For example, the processor may record a temperature near the patient's head, a temperature near the patient's torso, and a temperature for portions of the pad which are not in contact with the patient.

The one or more temperature sensors may be an NTC sensor (Negative Temperature Coefficient), whose resistance value decreases as temperature increases. The one or more temperature sensors may be a PTC sensor (Positive Temperature Coefficient), whose resistance value increases as temperature increases. he one or more temperature sensors may be a thermistor or thermocouple.

The top layer and the bottom layer may be made of foam. The top layer and the bottom layer may be made from the same foam material. In some configurations, the top layer and the bottom layer may be made from different materials or different foam. In some configurations, the top layer may be made of foam, and the bottom layer may be made of a different material that is not foam.

The top and/or bottom layers may be made from or comprise a viscoelastic foam. The rate of recovery, that is, the time required for a viscoelastic foam to return to its starting shape, is in the range of approximately 2-10 seconds for approximately 50 percent to 80 percent recovery after deformation caused by placing an adult torso on an approximately one inch thick layer of viscoelastic foam. The rate of recovery is in the range of approximately 6-15 seconds for approximately 80 percent to 90 percent recovery after deformation caused by placing an adult torso on an approximately one inch thick layer of viscoelastic foam. The rate of recovery is in the range of approximately 10-35 seconds for 100 percent recovery after deformation caused by placing an adult torso on an approximately one inch thick layer of viscoelastic foam. The ball rebound of the viscoelastic foam is in the range of less than or substantially less than approximately one percent to approximately one percent or several percent, or is in the range of or approximately in the range of 0.1 percent to 1.9 percent, or up to 3 percent or 5 percent, and as much as several percent. The compression set (the residual compression of the foam after twenty-two hours at seventy degrees Celsius) of the viscoelastic foam, for a 25 percent compression of the foam, is in the range of less than one percent or tenths of a percent, such as, for example, less than 0.4 percent or 0.3 percent, to several percent. The compression set of the viscoelastic foam, for a fifty percent compression of the foam, is in the range of less than one percent or tenths of a percent, such as, for example, less than 0.5 percent, to several percent. The indentation force deflection of the viscoelastic foam, at a 25 percent deflection, is in the range of several pounds of force to tens of pounds of force, such as in the range of approximately 10 to approximately 15 pounds, or in the range of approximately 7 to approximately 18 pounds, or is in the range of approximately 12 pounds, such as, for example, 11.7, 11.8, 11.9, 12.0, 12.1, 12.2, 12.3, and 12.4 pounds. The coefficient of static friction between the viscoelastic foam and the surface of a support table is greater than 0.2, or is in the range of approximately 0.2 or 0.5 to approximately 0.7 or 1.0. The viscoelastic foam is designed such that the patient may shift on the viscoelastic foam less than one inch, or up to approximately an inch, or in the range of approximately one inch to approximately three inches. The airflow in or through the viscoelastic foam is in the range of tenths of a cubic foot per minute to several cubic feet per minute, such as, for example, approximately 0.1 or 0.3 cubic foot per minute to approximately 1.0 or 3.0 cubic feet per minute, or is in the range of approximately 0.53 cubic feet per minute, plus or minus 0.3 cubic feet per minute. The thickness of the viscoelastic foam is in the range of from three-fourths of an inch to one inch, or to approximately one inch, or to one and a half inches, or to three inches or greater, which thickness is selected to minimize and/or prevent bottoming out on the operating table of one or more of the portions of the body of a patient lying on the viscoelastic foam pad, depending on the weight and/or size of the patient. The tensile strength (at 25 percent deflection) of the viscoelastic foam is in the range of at least approximately 5 pounds per square inch (PSI) or approximately 8 PSI to approximately 12 PSI or approximately 15 PSI, or is in the range of approximately 10 PSI. The tear strength (in a twenty inches per minute test) of the viscoelastic foam is in the range of approximately one to approximately two or three pounds of force per inch, or in the range of approximately 1.5 pounds of force per inch. The elongation (in a twenty inches per minute test) of the viscoelastic foam is in the range of between 125 and 250 percent, or is in the range of approximately 172 percent, plus or minus 25 percent. The nominal density of the viscoelastic foam is in a range of approximately 100 kilograms per cubic meter, or is in the range of approximately 75 or 83 kilograms per cubic meter to approximately 103 or 110 kilograms per cubic meter, such as, for example, 93.1 kilograms per cubic meter. The flammability of the viscoelastic foam should pass various tests by CAL, FMVSS and FAR, and the viscoelastic foam should pass the European Union's Restriction of Hazardous Substances (EU RoHS) standards. In one particular example, the viscoelastic foam comprises a viscoelastic polyurethane having one or more of: a ball rebound in the range of approximately 0.1 percent to approximately 1.9 percent; a compression set, for a 25 percent compression, of less than 0.5 percent; an air flow in the range of 0.3 to 1.0 cubic foot per minute; an indentation force deflection in the range of approximately 10 to approximately 15 pounds; a tensile strength in the range of approximately 8 pounds per square inch to approximately 12 pounds per square inch; a coefficient of static friction in the range of 0.2 to 1.0; and a density in the range of approximately 83 kilograms per cubic meter to approximately 103 kilograms per cubic meter. In some examples, a viscoelastic pad formed from viscoelastic polyurethane will have one or more of the following mechanical properties: a ball rebound in the range of approximately 0.1 percent to approximately 1.9 percent; a compression set (22 hrs@ 70° C.), for a 25 percent compression, of less than 0.5 percent (ASTM D-3574); an air flow in the range of 0.3 to 1.0 cubic foot per minute (ASTM D-3574); an indentation force deflection in the range of approximately 10 to approximately 15 pounds, and preferably about 11 pounds (ASTM D-3574); a tensile strength in the range of approximately 8 pounds per square inch to approximately 12 pounds per square inch; a coefficient of static friction in the range of 0.2 to 1.0; and a density in the range of approximately 83 kilograms per cubic meter to approximately 103 kilograms per cubic meter, and preferably about 93 kilograms per cubic meter (ASTM D-3574).

The top and/or bottom layers may be made from or comprise a non-viscoelastic foam. A suitable non-viscoelastic foam having a relatively high rate of recovery or the time at which the non-viscoelastic foam returns to its starting shape after being deformed. For example, a suitable material for the pad or one or more layers of the body disclosed herein may have a rate of recovery that is substantially faster than a rate of recovery of a viscoelastic foam. A rate of recovery of a suitable foam for the pad or one or more layers of the body disclosed herein may be one and a half seconds or less or one second or less, and in some embodiments may be substantially less than one second. For example, a rate of recovery may be high enough such that a measurement of the rate of recovery may be indeterminate or instantaneous due to the rapid rate at which the foam recovers to an original shape after being deformed. For instances in which the rate of recovery is indeterminate or instantaneous, the material recovers at the same speed as the indenter foot is removed after indentation such that contact between the material and the indenter foot is maintained. The non-viscoelastic foam may be formed from an active response polyurethane or air infused polyurethane comprised of a combination of toluene diisocyanate (TDI) and a high molecular weight polyol, such as those with a molecular weight from 2000 to 10,000, thereby allowing the pad or one or more layers of the body disclosed herein to be substantially pliable at a wide range of temperatures including low temperatures. A glass transition temperature of a suitable non-viscoelastic foam, such as a non-viscoelastic polyurethane foam, may be substantially less than a glass transition temperature of a viscoelastic foam. For example, a suitable non-viscoelastic foam may have a glass transition temperature of −20° C. or less and may be approximately −66° C. or less. A low glass transition temperature of a suitable non-viscoelastic foam allows the pad or one or more layers of the body disclosed herein to remain substantially pliable at a wider range of ambient temperatures relative to a viscoelastic foam. The non-viscoelastic foam forming the pad or one or more layers of the body disclosed herein may be resiliently deformable such that the non-viscoelastic foam may deform around a contour of a patient positioned on the medical table and the pad while retaining a high rebound rate to a non-deformed shape. Embodiments of the pad or one or more layers of the body disclosed herein may provide substantially instantaneous customized support to a shape of a patient laying thereon. Further, if a position of a patient shifts, the pad or one or more layers of the body disclosed herein may substantially instantaneously respond to such shifting such that the pad or body may rapidly contour to the patient in a new position of the patient. The non-viscoelastic foam may be formed having air capsules formed therein, such as microscopic air capsules formed within the non-viscoelastic foam that may be created during manufacturing of the non-viscoelastic foam. A suitable non-viscoelastic foam may further have suitable anti-skid properties to prevent sliding of a patient on a medical table. The non-viscoelastic foam may have a suitable coefficient of friction such that a patient does not slide along an operating table or other surface on which the pad or one or more layers of the body disclosed herein is located. In particular, when a patient is laying on the pad, the non-viscoelastic foam may be deformable and may interact with a surface of the medical table to prevent sliding of the patient and the pad on the table, even when the patient is at least partially inclined or declined on the operating table. A suitable coefficient of friction of the non-viscoelastic foam is such that the pad does not slide or otherwise substantially move against a surface of an operating table on which the pad is located, particularly when the operating table is at least partially inclined or declined with a patient thereon during a procedure. Further, embodiments of the pad herein may be such that a coefficient of friction of the non-viscoelastic foam substantially prevents sliding or movement of the pad on an operating table without requiring use of straps, tape, or other mechanisms required to prevent substantial sliding or movement.

In some configurations, one of the layers may be made from a viscoelastic foam and the other layer may be made from a non-viscoelastic foam. In some configurations, a portion of one of the layers may be made from a viscoelastic foam and another portion from a non-viscoelastic foam.

The one or more heating elements disclosed herein may comprise conductive bus bars that are electrically connected to a control device or power source. The conductive bus bars include a first conductive bus bar attached at or near one of the at least two side edges of the heating element and a second conductive bus bar attached at or near another of the at least two side edges of the flexible sheet-like heating element. The bus bars may be comprised of flattened tubes of braided wires, such as are known to those skilled in the art (e.g., a flat braided silver coated copper wire) and may thus accommodate the thread or heating elements extending therethrough, passing through openings between the braided wires thereof. The bus bars may be flexible to enhance the flexibility of the pad. The bus bars can be a conductive foil or wire, flattened braided wires not formed in tubes, an embroidery of conductive thread, or a printing of conductive ink. The bus bars may be flat braided silver-coated copper wire material, since a silver coating has shown superior durability with repeated flexion, as compared to tin-coated wire, for example, and may be less susceptible to oxidative interaction with a polypyrrole coating of heating element.

The one or more heating elements that extend between or electrically connect the bus bars. The one or more heating elements may be woven fibers or wires between the bus bars. The one or more heating elements may be arranged in a grid-like, lattice, or meandering pattern.

The explanations and illustrations presented herein are intended to acquaint others skilled in the art with the invention, its principles, and its practical application. The above description is intended to be illustrative and not restrictive. Those skilled in the art may adapt and apply the invention in its numerous forms, as may be best suited to the requirements of a particular use.

Accordingly, the specific embodiments of the present invention as set forth are not intended as being exhaustive or limiting of the teachings. The scope of the teachings should, therefore, be determined not with reference to this description, but should instead be determined with reference to the appended claims, along with the full scope of equivalents to which such claims are entitled. The omission in the following claims of any aspect of subject matter that is disclosed herein is not a disclaimer of such subject matter, nor should it be regarded that the inventors did not consider such subject matter to be part of the disclosed inventive subject matter.

Plural elements or steps can be provided by a single integrated element or step. Alternatively, a single element or step might be divided into separate plural elements or steps.

The disclosure of "a" or "one" to describe an element or step is not intended to foreclose additional elements or steps. For example, disclosure of "a motor" does not limit the teachings to a single motor. Instead, for example, disclosure of "a motor" may include "one or more motors."

While the terms first, second, third, etc., may be used herein to describe various elements, components, regions, layers and/or sections, these elements, components, regions, layers, and/or sections should not be limited by these terms. These terms may be used to distinguish one element, component, region, layer or section from another region, layer, or section. Terms such as "first," "second," and other numerical terms when used herein do not imply a sequence or order unless clearly indicated by the context. Thus, a first element, component, region, layer, or section discussed below could be termed a second element, component, region, layer, or section without departing from the teachings.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The invention illustratively disclosed herein suitably may be practiced in the absence of any element which is not specifically disclosed herein.

Any of the elements, components, regions, layers, and/or sections disclosed herein are not necessarily limited to a single embodiment. Instead, any of the elements, components, regions, layers, and/or sections disclosed herein may be substituted, combined, and/or modified with any of the elements, components, regions, layers, and/or sections disclosed herein to form one or more embodiments that may not be specifically illustrated or described herein.

The disclosures of all articles and references, including patent applications and publications, testing specifications, are incorporated by reference for all purposes. Other combinations are also possible as will be gleaned from the following claims, which are also hereby incorporated by reference into this written description.

The invention claimed is:

1. A patient warming pad configured for placement between a patient and a support surface of a medical table, the patient warming pad comprising:

a body comprising a top foam layer and a bottom layer, the top foam layer having an intended patient-contact region and an intended patient-non-contact region, the bottom layer having a support-contact region;

one or more straps for securing the body to the medical table;

a flexible sheet-like resistive heating device disposed between the top foam layer and the bottom layer, the flexible sheet-like resistive heating device comprising one or more resistive heating wires, the flexible sheet-like resistive heating device extending below at least a portion of the intended patient-contact region and the intended patient-non-contact region, the flexible sheet-like resistive heating device comprises a flexible substrate supporting a pair of spaced-apart flexible conductive bus bars arranged adjacent to opposing lateral sides of the substrate, the one or more resistive heating wires are electrically coupled to the pair of spaced-apart flexible conductive bus bars, the one or more resistive heating wires being configured to generate heat when electrical power is supplied to the flexible sheet-like resistive heating device; and one or more temperature sensors;

wherein the one or more temperature sensors are positioned on the flexible sheet-like resistive heating device such that the one or more temperature sensors are only located at the intended patient-non-contact region and not in the intended patient-contact region, wherein the patient warming pad comprises a head end, wherein the pair of spaced-apart flexible conductive bus bars terminate at a boundary defining a non-heated head-support zone at a location that is offset from the head end of the patient warming pad so that the non-heated head-support zone at the head end of the patient warming pad is free of the one or more resistive heating wires, and wherein positioning the one or more temperature sensors in the intended patient-non-contact region reduces compression-induced measurement error.

2. The patient warming pad according to claim 1, wherein the one or more temperature sensors are laterally offset from a longitudinal axis of the patient warming pad.

3. The patient warming pad according to claim 2, wherein the one or more temperature sensors are located above a shoulder region of the patient in a direction towards the head end of the patient warming pad when the patient is positioned on the intended patient-contact region.

4. The patient warming pad according to claim 2, wherein the one or more temperature sensors are located between a shoulder region and an ear region of the patient when the patient is positioned on the intended patient-contact region.

5. The patient warming pad according to claim 3, wherein the flexible sheet-like resistive heating device does not include a temperature sensor in a torso region of the patient, or the flexible sheet-like resistive heating device is free of temperature sensors in the torso region of the patient when the patient is positioned on the intended patient-contact region.

6. The patient warming pad according to claim 4, wherein the flexible sheet-like resistive heating device does not include any temperature sensors below the shoulder region of the patient in a direction towards a bottom or tail end of the patient warming pad when the patient is positioned on the intended patient-contact region.

7. The patient warming pad according to claim 6, wherein the body comprises opposing sides or edges, and the one or more temperature sensors are arranged approximately 5 cm from the opposing sides or edges.

8. The patient warming pad according to claim 7, wherein a head of the patient is configured to be placed adjacent the head end of the patient warming pad, and wherein the one or more temperature sensors are arranged more than approximately 247 mm from the head end of the patient warming pad.

9. The patient warming pad according to claim 8, wherein the one or more temperature sensors comprise one or more negative temperature-coefficient (NTC) temperature sensors.

10. The patient warming pad according to claim 6, wherein the one or more temperature sensors comprise exactly two temperature sensors, and the exactly two temperature sensors are arranged symmetrically on opposite sides of the longitudinal axis of the patient warming pad.

11. The patient warming pad according to claim 1, wherein the flexible sheet-like resistive heating device comprises one or more carbon filaments or carbon strands.

12. The patient warming pad according to claim 1, wherein the top foam layer, the bottom layer, or both of the top foam layer and the bottom layer comprise a viscoelastic foam.

13. The patient warming pad according to claim 1, wherein the top foam layer, the bottom layer, or both of the top foam layer and the bottom layer comprise a non-viscoelastic foam.

14. The patient warming pad according to claim 1, wherein the bottom layer comprises foam.

15. A method of making the patient warming pad according to claim 1, the method comprising:

forming the body comprising the top foam layer and the bottom layer, the top foam layer defining the intended patient-contact region and the intended patient-non-contact region, and the bottom layer defining the support-contact region;

providing the one or more straps for securing the body to the medical table;

providing the flexible, sheet-like resistive heating device;

positioning the flexible, sheet-like resistive heating device between the top foam layer and the bottom layer such that the pair of spaced-apart flexible conductive bus bars terminate at the boundary defining the non-heated head-support zone; and the one or more temperature sensors are located at the intended patient-non-contact region and not in the intended patient-contact region to avoid creating localized pressure points under the patient.

16. The method according to claim 15, wherein the positioning the flexible, sheet-like resistive heating device comprises locating the one or more temperature sensors laterally offset from a longitudinal axis of the flexible, sheet-like resistive heating device.

17. The method according to claim 16, wherein the one or more temperature sensors are located above a shoulder region of the patient in a direction of the head end of the patient warming pad when the patient is positioned on the intended patient-contact region.

18. The method according to claim 17, wherein the one or more temperature sensors are between the shoulder region and an ear region of the patient when the patient is positioned on the intended patient-contact region.

19. The patient warming pad according to claim 1, wherein the patient warming pad comprises a tail end at an end of the patient warming pad that opposes the head end, the tail end comprises a U-shaped perineal cutout, and wherein the one or more resistive heating wires are arranged in a grid-like, lattice, or meandering pattern.

* * * * *